Figure 1:
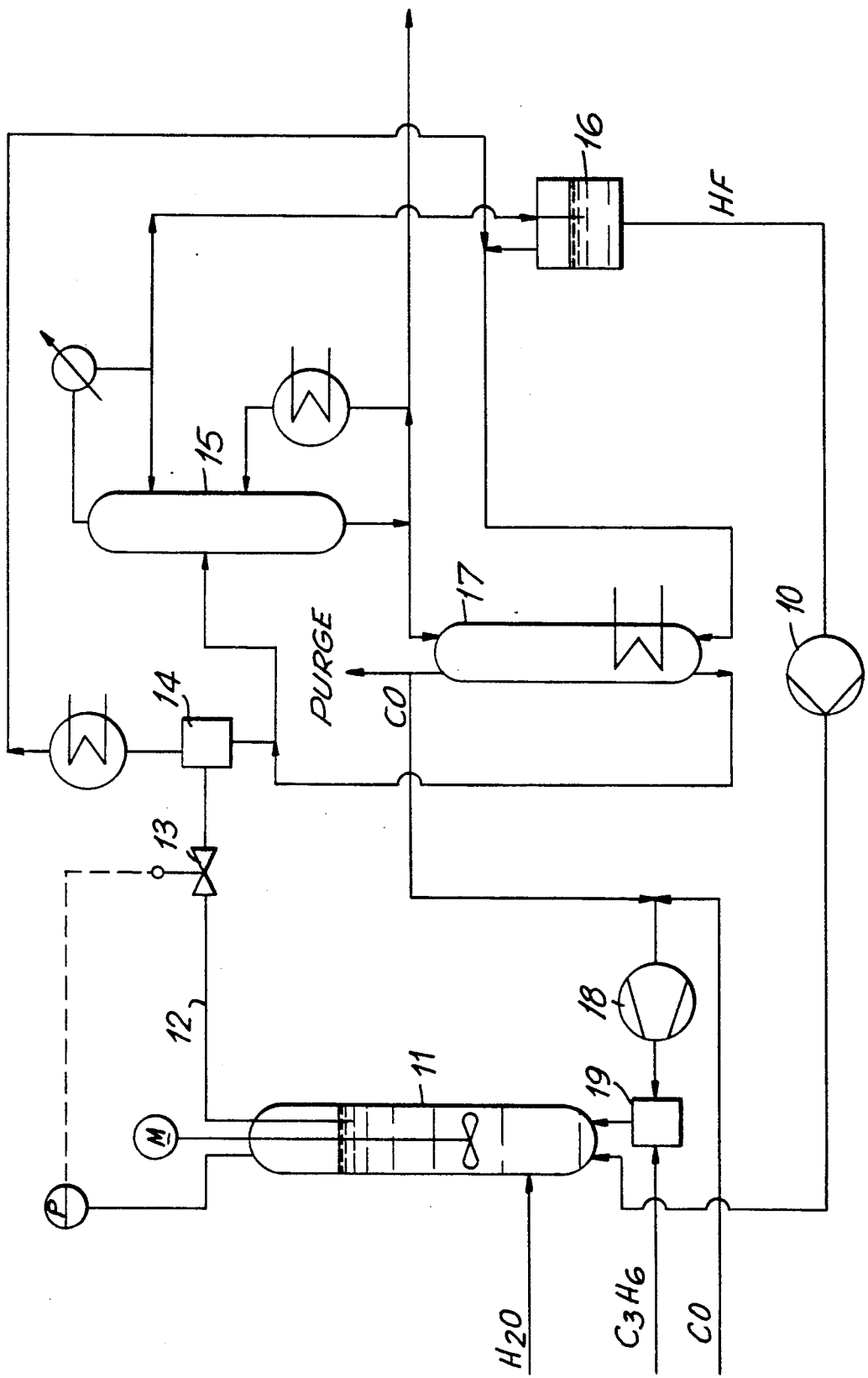

United States Patent [19]
Ruppert et al.

[11] Patent Number: 5,169,985
[45] Date of Patent: Dec. 8, 1992

[54] CONTINUOUS METHOD FOR MAKING ISOBUTYRIC ACID

[75] Inventors: Wolfgang Ruppert, Bickenbach; Willi Ploesser, Seeheim-Jugenheim, both of Fed. Rep. of Germany

[73] Assignee: Röhm GmbH, Darmstadt, Fed. Rep. of Germany

[21] Appl. No.: 873,884

[22] Filed: Apr. 24, 1992

Related U.S. Application Data

[63] Continuation of Ser. No. 700,069, May 3, 1991, abandoned, which is a continuation of Ser. No. 464,902, Jan. 16, 1990, abandoned.

[30] Foreign Application Priority Data

Jan. 25, 1989 [DE] Fed. Rep. of Germany ....... 3902104

[51] Int. Cl.$^5$ ................. C07C 53/24; C07B 53/00
[52] U.S. Cl. ................................. 562/521; 560/233
[58] Field of Search .................. 562/521; 560/233

[56] References Cited

U.S. PATENT DOCUMENTS

| | | | |
|---|---|---|---|
| 4,452,999 | 6/1984 | Besecke et al. | 560/233 |
| 4,504,675 | 3/1985 | Besecke et al. | 560/233 |
| 4,647,696 | 3/1987 | Besecke et al. | 562/606 |
| 4,791,227 | 12/1988 | Neumann et al. | 562/521 |

OTHER PUBLICATIONS

Kirk-Othmer, Encyclopedia of Chemical Technology, vol. 10, p. 735 (1982).

Primary Examiner—Arthur C. Prescott

[57] ABSTRACT

Methods of improving the yield in the continuous preparation of isobutyric acid from propene, carbon monoxide, and water under pressure in liquid hydrogen fluoride as a Koch catalyst by mixing the propene with excess carbon monoxide, preferably carbon monoxide reintroduced from the process and freed of HF, and introducing the mixture into the reactor.

5 Claims, 2 Drawing Sheets

CONTINUOUS METHOD FOR MAKING ISOBUTYRIC ACID

This application is a continuation of application Ser. No. 07/700,069 filed May 31, 1991 and now abandoned, which in turn is a continuation of application Ser. No. 07/464,902 filed Jan. 16, 1990 and now abandoned.

The present invention relates to a method for the continuous preparation of isobutyric acid or an ester thereof by the Koch synthesis from propene, carbon monoxide, and water or a lower alcohol in hydrogen fluoride as a Koch catalyst.

A method of the aforementioned kind is known from DE-C 30 33 655, in which the starting materials are introduced from time to time through separate lines into the reactor. The mol ratio of the amounts of propene and carbon monoxide introduced, optionally together, is 1:1.5. No influence of this mixing ratio on the yield can be recognized. At a dwell time of 5 minutes, a yield of 91 to 92 percent of isobutyric acid is reached in a laboratory reactor at 120° C. at a pressure of 120 bar of CO and with a ratio of 10 mols of hydrogen fluoride per mol of propene as the ratio of introduction. If the reaction is carried out in an industrial reactor under the same conditions, the yield decreases to 88 to 89 percent.

The object of the present invention is to increase the yield of isobutyric acid while maintaining the remaining reaction conditions. It has been found that the yield increases if the fresh, introduced, propene is mixed with more than 1.5-fold the molar amount of carbon monoxide and introduced into the reaction. In the aforementioned industrial reactor, an increase in the yield to 94 percent was attained using these measures at a mol ratio of CO:propene of 4:1.

The most advantageous ratio of carbon monoxide to propene is between 1.8:1 to 15:1, particularly to 10:1. No further improvement in the yield is attained with a further increase of carbon monoxide in the gas stream, but the economy decreases. In the reaction of the starting materials, carbon monoxide is consumed at the most in an equimolar ratio to propene, so that a portion of the gas phase containing the excess carbon monoxide must be continuously led out of the reactor. The method can then only be performed economically if the unused carbon monoxide is compressed and reintroduced into the process.

The gas phase taken off at first consists of a mixture of carbon monoxide and hydrogen fluoride, as well as, possibly, small amounts of propane, water, and gaseous by-products. If the gas mixture is reintroduced into the process in its entirety, the aforementioned impurities are enriched in the gas phase and for this reason are removed by continuous separation of a portion of the gas phase.

For economic reasons, it seemed at first to make sense to mix the propene to be introduced with carbon monoxide which is reintroduced as a replacement for the carbon monoxide consumed without prior purification of the carbon monoxide to remove hydrogen fluoride, since the carbon monoxide would in any event be mixed again with hydrogen fluoride on introduction into the reactor. Nevertheless, it has proved that on mixing propene with carbon monoxide contaminated with hydrogen fluoride, polymerization of the propene in the mixing chamber occurs. The loss of propene brought about in this way is so large that the yield of isobutyric acid falls to less than 70 percent.

It has been determined that polymerization of the propene is initiated by the hydrogen fluoride content of the gas mixture. Only at a content of hydrogen fluoride below 5 mol percent, preferably below 3 mol percent, in the gas mixture does the polymerization decrease to a negligible amount. Preferably, the HF-content should not be more than 1 mol percent.

In a preferred embodiment of the invention, thus, the carbon monoxide reintroduced is freed of hydrogen fluoride. Suitably, the latter is removed by washing with a liquid which absorbs hydrogen fluoride. Water can be used as the absorbing liquid, which, however, is often disadvantageous because of the high corrosiveness of the hydrofluoric acid formed. Preferably, isobutyric acid is used as the absorbing liquid, since it has a high binding capacity for hydrogen fluoride. The mixture which is formed by the absorption is less corrosive and can be worked up together with the stream leaving the reactor. It is not necessary to use pure isobutyric acid for absorption. For example, one can use the stream leaving the sump of that distillation in which hydrogen fluoride is distilled off from the liquid reaction mixture. This sump fraction consists predominately about 80 to 99 percent by weight) of isobutyric acid together with compounds formed in the reaction which have high boiling points.

Figure 2:
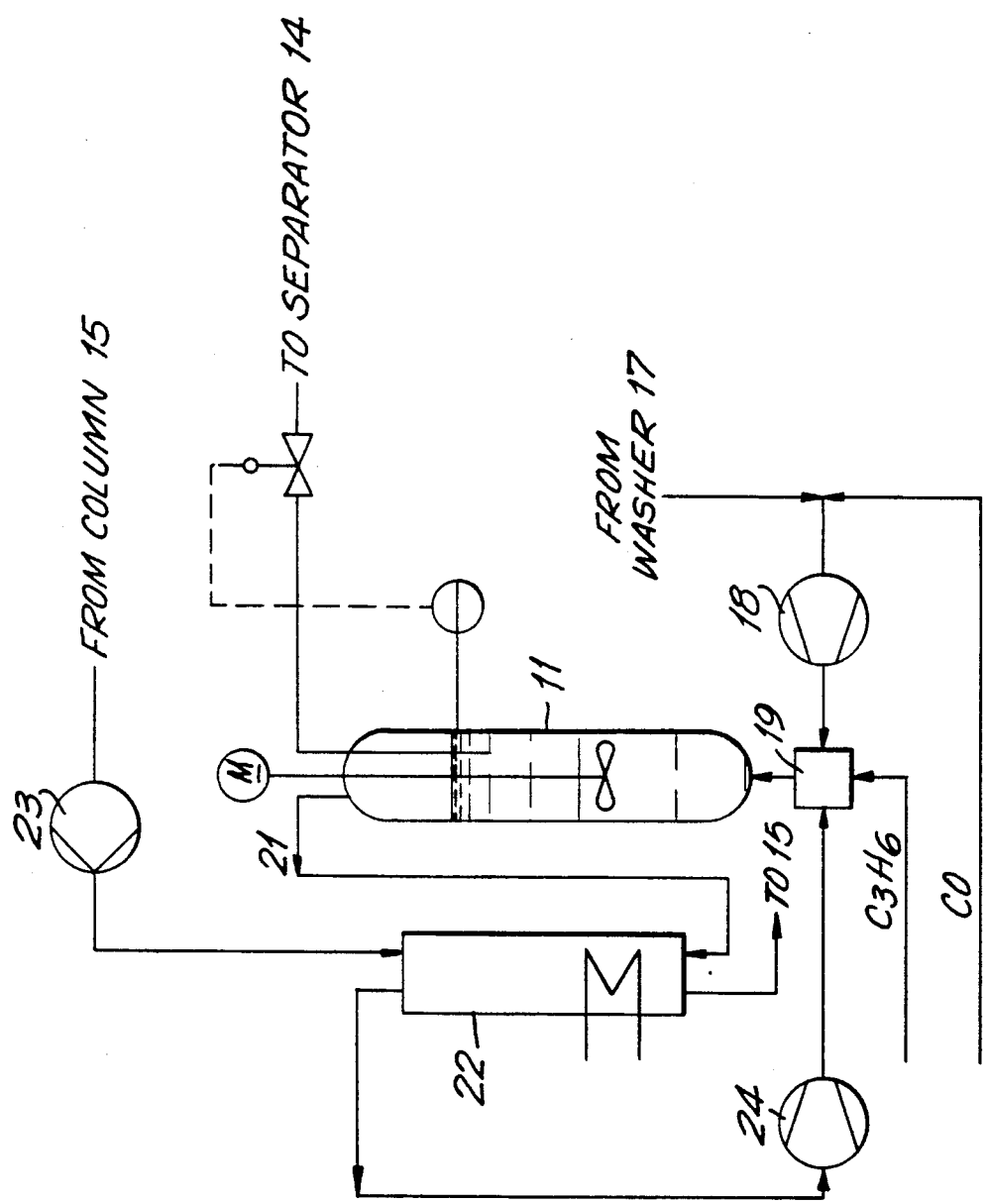

In the accompanying drawings, FIGS. 1 and 2 are flow diagrams illustrating suitable arrangements for performing the method of the invention.

More in particular, FIG. 1 shows a method variant in which the gas phase removed from the reactor is expanded, purified, compressed, and then mixed under pressure with propene. FIG. 2 pertains to method variant in which the principal portion of the gas phase is purified under pressure and mixed with propene without expansion and reintroduced into the reactor.

Thus, in the arrangement of FIG. 1, liquid and gaseous reaction mixture is removed from reactor 11 through the pipe 12 so that the liquid level stands at the lower end of pipe 12. The pressure of the reaction mixture removed is reduced from about 50 to 100 bar, preferably 100 to 140 bar to about 1 to 5 bar at expansion valve 13. One can also expand in several pressure steps, in each case separating a portion of the gas phase. The gaseous portion is separated in separator 14. The liquid fractions are separated in distillation column 15 into a distillate predominately consisting of hydrogen fluoride and a sump stream which consists of 80-99 percent by weight of isobutyric acid and a remainder of compounds having high boiling points. The distillate is led to intermediate container 16 where the remaining carbon monoxide separates from the liquid hydrogen fluoride. The gas phases removed from the containers 14 and 16 are purified and led to countercurrent washer 17 where the hydrogen fluoride is washed out with a portion of the sump stream from column 15. The heat of absorption can be removed by cooling. The amount of the wash liquid should be so chosen that the HF-content in the exiting wash liquid is in the range from 1 to 50 percent by weight. If, for example, the gas phase consists of 85 percent of carbon monoxide and of 15 percent of hydrogen fluoride, 2 to 95 percent of the total stream removed from the sump is led to washer 17. The gas streaming from washer 17 has an HF-content of only 0.5 percent by weight.

A portion of the purified gas phase, e.g. 2 percent, is separated in order to remove impurities from the cycle. The main portion of the gas phase is combined with fresh carbon monoxide and compressed in compressor 18 to the reaction pressure of 50 to 40 bar, preferably of 100 to 140 bar and mixed in mixing chamber 19 with fresh propene. In order to maintain a gaseous condition, the temperature of the mixture is adjusted to at least 70° C. The gas mixture is then led into reactor 11. At the same time, liquid hydrogen fluoride is led into the reactor from container 16 by way of the pump 10.

In the method variant shown in FIG. 2, the main portion of the gas phase is led through conduit 21 into pressure washer 22, where it is purified of hydrogen fluoride in countercurrent with the wash liquid, and introduced into mixing chamber 19 by means of blower 24. If a jet stream reactor is used as reactor 11, the CO gas cycle can be propelled by way of one or more jet pumps in which two materials are mixed and expelled. In this case, blower 24 is unnecessary. The wash liquid is brought to the operating pressure of 50 to 140 by means of pump 23 and led to the head of washer 22. If the stream exiting from the sump of column 15 is used as the wash liquid, then the wash liquid, loaded with hydrogen fluoride, is led back to column 15 after expansion. The remaining portion of the arrangement corresponds to the scheme of FIG. 1.

The variant shown in FIG. 2 is particularly advantageous at a high ratio of carbon monoxide to propene, for example greater than 4:1.

Instead of an extraction using a wash liquid, at high pressures, for example over 100 bar, the hydrogen fluoride can be condensed and its fraction in the gas phase sufficiently decreased thereby. In this case, washer 22 is replaced by a condenser. If, for example, the content of hydrogen fluoride in the gas streaming through pipe 21 is 15 percent, the HF-content in the gas can be reduced to 0.8 percent by cooling to 20° C. to 30° C.

A better understanding of the present invention may be had be referring to the following Example, given by way of illustration.

EXAMPLE 1

Propene, carbon monoxide, water, and hydrogen fluoride in a mole ratio of 1:1.3–2.8:0.8–1.0:10 are continuously reacted in a stirred autoclave of 1.6 liter capacity at 120° C., a pressure of 120 bar, and a stirring speed of 1,500 revolutions per minute (rpm). Propene and carbon monoxide, both free of HF, are mixed before being fed into the autoclave. Depending on the composition of this gas mixture, the following yields (as percent of theory based on propene) are achieved:

| Test No. | Mole Ratio CO:Propene | Yield Isobutyric Acid | Oligomer Formation |
|---|---|---|---|
| 1 | 1.9:1 | 90.5% | 6% |
| 2 Comparison Test | 2.8:1 | 93.5% | 5% |

-continued

| Test No. | Mole Ratio CO:Propene | Yield Isobutyric Acid | Oligomer Formation |
|---|---|---|---|
| 1 | 1.3:1 | 81.5% | 5% |

EXAMPLE 2

Using an apparatus as in Example 1, a mixture of propene, CO, water, and HF in a mol ratio of 1:3.4:1:9.6 are reacted at 120° C. and 120 bar, stirred at 1500 rpm. The CO introduced contained 0.5–1.0 mol percent of HF. In a comparison test in which the ratio of CO:propene was 5.9:1, HF content in the CO was 20 percent.

| HF-content in CO (Mol %) | Mol Ratio CO:Propene | Dwell Time (minutes) | Yield % |
|---|---|---|---|
| 0.5–1 | 3.4:1 | 4.6 | 89.6 |
| 20 | 5.9:1 | 5.7 | 67.4 |

What is claimed is:

1. A method for the continuous preparation of isobutyric acid or a lower alkyl ester thereof, respectively, in a pressure reactor by the Koch synthesis from a reaction mixture consisting of propene, carbon monoxide, water or a lower alkanol, respectively, and hydrogen fluoride as a Koch catalyst, which method comprises
   a) continuously introducing water or a lower alkanol and hydrogen fluoride into said reactor;
   b) continuously reacting said reaction mixture within said reactor;
   c) continuously removing said reaction mixture from said reactor;
   d) continuously recovering a gaseous component from the reaction mixture removed from said reactor;
   e) continuously removing hydrogen fluoride from said gaseous component to produce a gas containing carbon monoxide and less than 5 mole percent of hydrogen fluoride;
   f) continuously introducing fresh carbon monoxide into said gas;
   g) continuously mixing the gas mixture of step f) with fresh propene at a mole ratio of carbon monoxide to propene between 1.8:1 and 15:1; and
   h) continuously introducing the gas mixture of step g) into the reactor.

2. A method as in claim 1, wherein said gaseous component is freed of hydrogen fluoride by washing with an absorption liquid.

3. A method as in claim 2 wherein said absorption liquid is water.

4. A method as in claim 2 wherein said absorption liquid comprises isobutyric acid.

5. A method as in claim 4 wherein hydrogen fluoride is recovered from a liquid portion of said removed reaction mixture by distillation leaving a sump fraction consisting predominately of isobutyric acid, and wherein said sump fraction is used as said absorption liquid.

* * * * *